United States Patent [19]

Jouy et al.

[11] 3,994,833

[45] Nov. 30, 1976

[54] OXIDATION CATALYST AND PROCESS FOR ITS PREPARATION

[75] Inventors: Marcel Jouy, Saint-Cyr l'Ecole; Francis Van Den Bussche, Ris Orangis, both of France

[73] Assignee: Rhone-Progil, Courbevoie, France

[22] Filed: Nov. 21, 1974

(Under Rule 47)

[21] Appl. No.: 525,881

[30] Foreign Application Priority Data

Nov. 22, 1973  France ............................ 73.41573

[52] U.S. Cl. ...................... 252/469; 260/346.8 A
[51] Int. Cl.² .................. B01J 23/28; B01J 23/34; B01J 21/06; B01J 23/88
[58] Field of Search ............... 252/469; 260/346.8 A

[56] References Cited
UNITED STATES PATENTS

| 2,365,895 | 12/1944 | Mavity | 252/469 X |
| 2,605,238 | 7/1952 | Krantz | 260/346.8 A |
| 3,086,026 | 4/1963 | Wiebusch | 260/346.8 A |
| 3,867,412 | 2/1975 | Barker | 260/346.8 A |

FOREIGN PATENTS OR APPLICATIONS

| 1,248,508 | 11/1960 | France | 260/346.8 A |

*Primary Examiner*—W. J. Shine
*Attorney, Agent, or Firm*—McDougall, Hersh & Scott

[57] ABSTRACT

The object of the invention is a catalyst for oxidizing organic compounds. The catalyst is characterized by the fact that the active material consists of molybdenum oxide deposited on anatase type titanium dioxide. The catalyst can be used for the oxidation of organic compounds in order to obtain maleic anhydride.

9 Claims, No Drawings

OXIDATION CATALYST AND PROCESS FOR ITS PREPARATION

The object of the invention is a catalyst and a process for the oxidation of hydrocarbons, the oxidation being carried out with oxygen or a gaseous mixture containing oxygen, in a fixed bed, and at a high temperature. In particular, the invention is concerned with the manufacture of maleic anhydride.

A well known process for the manufacture of maleic anhydride consists in oxidizing benzene, in a fixed bed reactor, at about 350°–500° C in the presence of a catalyst formed from vanadium oxide and various additives deposited on a support.

It is also well known that maleic anhydride can be produced by oxidizing an unsaturated hydrocarbon containing at least 4 carbon atoms, such oxidation being carried out in the presence of a catalyst comprising vanadium oxide. However, although vanadium oxide is used as catalyst, the yield of maleic anhydride is not sufficiently high for industrial use. In order to improve the yield of maleic anhydride, in the case where a catalyst comprising vanadium oxide is used, a procedure is generally adopted which consists of adding a co-catalyst such as a molybdenum oxide, a tungsten oxide and a phosphorus oxide to the catalyst. For example, a catalyst comprising vanadium pentoxide and oxides of phosphorus and tungsten is described in Japanese patents. In this case, there is the disadvantage that the process must be operated under high air/butene ratios.

Studies have also been carried out on a catalyst for the production of maleic anhydride by oxidizing an unsaturated hydrocarbon containing at least 4 carbon atoms, based on tungsten as the catalyst component and phosphorus as the co-catalyst component, that is to say, using a catalyst comprising oxides of tungsten and phosphorus.

In this case, it was claimed that it was possible to obtain maleic anhydride in a high yield and without any decrease in calalytic activity during the reaction if there is present in the catalyst, comprising tungsten and phosphorus oxides, at least one compound (a third component) selected from the group consisting of an alkali metal compound, an alkaline earth metal compound, a copper compound, a zinc compound, a molybdenum compound, a chromium compound, a bismuth compound and a titanium compound, the amount of additive being of the order of 1 to 3%. In general, catalysts of this type do not have sufficient productivity.

Applicants have discovered a molybdenum-based catalyst which has much improved qualities and is free from the disadvantages of the aforementioned catalysts.

In accordance with the invention, the catalyst for oxidizing organic compounds contains a molybdenum oxide as the active material and is characterized by the fact that it comprises, by weight, 80 to 90% of titanium dioxide $TiO_2$, anatase type, having a specific surface between 5 and 20 $m^2/g$, and 8 to 20% of molybdenum oxide expressed as $MoO_3$.

In accordance with one variation, the catalyst for oxidizing organic compounds containing a molybdenum oxide as the active material is characterized by the fact that it comprises, by weight, 80 to 90% of anatase type titanium dioxide $TiO_2$ having a specific surface between 5 and 20 $m^2/g$, 8 to 18.5% of molybdenum oxide expressed as $MoO_3$, and 1.5 to 5% of an oxide of an element selected from the group consisting of chromium, antimony, bismuth, iron, nickel, tungsten, uranium, the atomic ratio of molybdenum to the element added being between 1 and 10.

In accordance with a more particular method of operation, the catalyst according to the invention for oxidizing organic compounds contains, by weight, 85 to 90% of anatase type $TiO_2$ support having a specific surface measured according to the BET method of between 5 and 10 $m^2/g$, 8 to 13.5% of molybdenum oxide expressed as $MoO_3$, and 1.5 to 5% of uranium expressed as $UO_3$, the weight ratio $TiO_2/MoO_3$ having a value between 7 and 12, and the atomic ratio molybdenum/uranium having a value between 1 and 10.

The object of the invention is also a process for oxidizing organic substances using the described catalyst in a fixed bed or in a fluidized bed.

In accordance with a more particular method of operation, the invention is directed to a process for producing maleic anhydride by oxidation with a fixed bed catalyst, characterized by the fact that organic compounds containing at least 4 carbon atoms are oxidized using the catalyst described above and operating at temperatures between 380° and 450° C, the molar ratios air/substance to be oxidized being between 40 and 100.

In accordance with one variation, the process is operated under a pressure greater than atmospheric pressure, between 1 and 30 $kg/cm^2$ and preferably between 1 and 10 $kg/cm^2$. More particularly, the invention is directed to a process for manufacturing maleic anhydride by oxidation, using a fixed bed catalyst, characterized by the fact that a $C_4$ hydrocarbon fraction is oxidized by air using the above-described catalyst and operating under a pressure between 1 and 10 $kg/cm^2$ and at temperatures between 380° and 450° C, with an oxygen/butene molar ratio between 8 and 20, i.e. an air/butene molar ratio between 40 and 100.

The object of the invention is also a process for preparing a fluidized bed catalyst, consisting in forming a paste from water and molybdenum derivatives soluble in water, uranium salts, oxalic acid and pigment quality anatase, drying the said paste, calcining the resultant product and then grinding and sieving the ground product to obtain the fraction having the appropriate grain size, for example between 250 and 500 microns.

According to another method of operation, with a view to preparing a fixed bed catalyst, the above procedure is carried out but the sieving is performed so as to collect a fraction having a size of 3–5 mm.

In order to obtain catalyst which can be used in a fixed bed, in accordance with a variation of the said manufacturing process, the above paste is applied in the form of pellets and is dried and calcined.

According to another method of operation for manufacturing the catalyst for the fixed bed, the above paste is extruded in cylindrical form and is dried and calcined.

The oxidation process, according to the invention, can be applied to a large number of reactions, such as the conversion of hydrocarbons to aldehydes, ketones and acids. In particular, maleic anhydride can be produced by vapor phase oxidation of organic compounds selected from the group comprising saturated or unsaturated hydrocarbons with at least four carbon atoms, such as butene, butene isomers, butadiene, cyclopentadiene, pentene, C₄ fractions obtained by cracking heavy petroleum, naphtha type compounds, benzene, toluene, naphthalene, methylnaphthalene, phenol, cresol, benzophenone, furan, biphenyl, furfural, heptane, isooctane, crotonaldehyde and crotonic acid.

As molybdenum derivatives which may be used for preparing the catalyst, the salts or other derivatives which are soluble in water may be mentioned. Ammonium heptamolybdate is preferably used.

As regards uranium derivatives which may be used according to the invention, the salts or other derivatives which are soluble in water may be mentioned; uranyl nitrate is preferably used.

As regards an additive other than uranium, any convenient water-soluble derivative may likewise be used, for example ammonium tungstate, chromium nitrate, nickel nitrate, manganese nitrate and ferric nitrate.

As anatase type titanium dioxide support, the so-called pigment quality material is used, that is to say having a specific surface measured according to the BET method of between 5 and 20 m²/g.

In the description and examples, which are given by way of example and are not limitative, the following abbreviations which are commonly used in the art will be employed:

MA for maleic acid
MAA for maleic anhydride

Definitions are given hereinafter for the various expressions such as "% weight yield", "molar % yield", "conversion rate", "selectivity", as well as the relationships between certain of these expressions.

Thus, in the case of the oxidation of butene:

a) Yields $$MAA \text{ \% weight yield} = \frac{\text{weight of } MAA \text{ formed}}{\text{weight of butene injected}} \times 100$$

$$MAA \text{ molar \% yield} = \frac{\text{number of moles of } MAA}{\text{number of moles of butene injected}} \times 100$$

There exists the following relationship between these two expressions:

$$MAA \text{ weight yield} = \text{molar yield} \times \frac{98}{56}$$

$$MA \text{ weight yield} = \text{molar yield} \times \frac{116}{56}$$

b) Conversion rate $$\text{Molar conversion rate} = \frac{\text{number of moles of butene oxidized}}{\text{number of moles of butene injected}} \times 100$$

c. Selectivity

There are several definitions of this expression. The selectivity which, it would appear, actually has to be used, and which will be termed molar or normal or correct selectivity, is defined as follows:

$$Sm = \frac{MAA \text{ molar yield} + \text{molar \% of relevant intermediates}}{\text{molar conversion rate for the whole of the normal butenes}} \times 100$$

By the expression relevant (valorizable) intermediate is understood all the species other than hydrocarbons contained in the starting fraction and which can be recovered and converted into MAA. In other words, essentially furane and butadiene. (In the case of butadiene the increase with respect to the starting amount will be taken into account.)

A. CATALYST PREPARATION

Examples of various catalysts will be given hereinafter, and since the preparation of these catalysts is well known to the person skilled in the art, only absolutely necessary information will be given for the sake of brevity.

In the preparation examples, the catalysts are differentiated by the percentage of material having catalytic activity, by the nature of the said active material, or by the type of support.

Next will be described, by way of example, the conditions under which the said catalysts are used, and the results obtained will be given in the form of tables.

EXAMPLE 1

This example relates to the preparation of a catalyst containing a catalytically active molybdenum oxide material on 34 m²/g anatase.

620 g of ammonium heptamolybdate and a sufficient amount of water are added to a beaker provided with a stirrer. The mixture is stirred until it has dissolved and then 340 g of oxalic acid crystals are added.

1 kg of anatase having a specific surface area of 34 m²/g is then added while stirring, to the resultant solution.

After thoroughly mixing for ½ hour the mixture is dried and calcined for 24 hours at 460° C.

The product obtained is then ground and sieved.

The grinding is more or less vigorous depending on the desired grain size, which is a function of the method of use. For example, for use in a fixed bed a fraction having a grain size of 3–5 mm is desired, whereas for a fluidized bed a grain size of 300–400 microns is desired.

The catalyst obtained under these conditions contains 66.5% TiO₂ and 33.5% MoO₃.

This catalyst is used to oxidize butenes in order to obtain maleic anhydride. The details of the operating conditions and the results are given later, together with those for other catalysts.

EXAMPLE 2

The procedure of Example 1 is followed except that the amount of heptamolybdate is reduced so as to obtain a catalyst having the composition TiO₂ 80%, MoO₃ 20%.

EXAMPLE 3

The procedure of Example 1 is repeated, with the exception that an anatase having a specific surface area of 7 m²/g, so-called pigment anatase, is used.

In this case 132 g of heptamolybdate and 71 g of oxalic acid are used, the amounts of the other reactants being the same, and a catalyst having the composition $TiO_2$ 90.3%, $MoO_3$ 9.7%, is obtained.

EXAMPLE 4

The method of preparing the catalyst described in Example 3 (anatase 7 m²/g) is repeated, except that the amount of heptamolybdate is altered so as to obtain a catalyst containing $TiO_2$ 93.5% and $MoO_3$ 6.7%.

EXAMPLE 5

This example relates to the preparation of a particularly interesting catalyst according to the invention, that is to say a catalytically active molybdenum-uranium material deposited on anatase form of titanium oxide $TiO_2$.

139 g of ammonium heptamolybdate and 1 liter of water are added to a beaker equipped with a stirrer, the whole is stirred until dissolved, and a solution of 39.5 g of uranyl nitrate in 500 cm³ of water, followed by 75 g of oxalic acid crystals, are then added. 1 kg of pigment quality anatase $TiO_2$ (that is to say an anatase having a specific surface area of 7 m²/g as measured by the BET method) is then added to this solution.

After mixing thoroughly for ½ hour, the mixture is dried and then calcined for 24 hours at 460° C. The resultant solid product is then ground. The ground product is sieved and the fraction having a grain size of 3 to 5 mm, which can be used in a fixed bed, is collected. For the fluidized bed catalyst the product is ground and the 300–400 micron size fraction is collected.

The catalyst has the following composition: $MoO_3$ 10%, $UO_3$ 2%, $TiO_2$ 88%. The atomic ratio of molybdenum to uranium is 10.

A series of examples employing different additives is given hereinafter.

In all the examples of additives given hereinafter, the molybdenum/metal additive atomic ratio is 10.

EXAMPLE 6

The procedure of Example 5 is followed except that the amount of uranyl nitrate is replaced by the equivalent amount of ammonium tungstate.

A catalyst containing $TiO_2$ 88%, $MoO_3$ 10.3%, $UO_3$ 1.65% is obtained.

EXAMPLE 7

A molybdenum oxide active material catalyst containing a chromium oxide additive is prepared following the procedure described in Example 5. During the preparation the uranyl nitrate is replaced by chromium nitrate. The catalyst obtained has the composition $TiO_2$ 88%, $MoO_3$ 11.4%, $Cr_2O_3$ 0.6%.

EXAMPLE 8

The method of preparation described in Example 5 is followed, the uranyl nitrate being replaced by nickel nitrate; the atomic ratio of molybdenum to nickel remains equal to 10. The catalyst thus consists of 88% $TiO_2$, 11.4% $MoO_3$ and 0.6% NiO.

EXAMPLE 9

A molybdenum oxide/manganese oxide catalyst is prepared following the described process, but incorporating manganese nitrate in place of uranyl nitrate in order to obtain a catalyst containing 88% $TiO_2$, 11.4% $MoO_3$ and 0.6% $Mn_2O_3$.

EXAMPLE 10

This example deals with the preparation of a catalyst containing 88% $TiO_2$, 11.4% $MoO_3$ and 0.6% $Fe_2O_3$.

The procedure of Example 5 is used, but ferric nitrate is employed in place of uranyl nitrate.

In order to give some comparison results obtained when using catalysts containing, in the active material, vanadium, which is generally considered to be necessary in oxidation processes intended to produce phthalic or maleic anhydride, two examples of these catalysts will now be given.

EXAMPLE 11

The purpose of this example is to compare catalysts containing vanadium and molybdenum, the latter being an additive with respect to vanadium. A catalyst containing 90.2% $TiO_2$, 7.1% $V_2O_5$ and 2.4% $MoO_3$ is prepared from ammonium heptamolybdate and ammonium metavanadate following the usual techniques.

EXAMPLE 12

As is well known in this technique, a vanadium-phosphorus active material catalyst is prepared, containing 86% $TiO_2$, (anatase having a specific surface area of 7 M²/g), 4% $V_2O_5$ and 10% $P_2O_5$.

B. OXIDATION PROCEDURE

EXAMPLE 13

The process described here relates to use in a fluidized bed. This process is used when, in a study, it is desirable to have the chance of changing the catalyst quickly, for example when investigating the best catalytic composition before studying the influence of the support, grain size or other factors. In particular, this procedure is used to decide on the final choice, taking into account the selectivity. The object of these tests is thus to study the selectivity of the catalytic materials, the yields obtained being generally less than those of the fixed bed.

A fluidized bed reactor is used, comprising a cylindrical tube 165 mm long with an internal diameter of 20 mm, and equipped with means for controlling the temperature to less than 1° C. The base of the reactor contains a "No. 1 frit" (frit glass plate allowing a gaseous fluid to enter the reactor) 20 mm in diameter. 20 cm³ of catalyst prepared according to Examples 1 to 11 and having a grain size of 300–400 microns are added to the reactor in separate tests. The air/butene or air/$C_4$ fraction mixture is passed through the frit at a flow rate and temperature suitable for the test.

As usual, the maleic anhydride present in the gas leaving the reactor is measured, and this is the value which will be used in the various calculations. The results and operating conditions corresponding to the use of catalysts in accordance with this fluidized bed technique are given in Table I hereinafter.

EXAMPLE 14

This example deals with the use of catalyst in tablet or granulated form in a fixed bed reactor.

When this method of operation is used, an effort is made to carry out the reaction to completion, that is to say to a conversion of about 100%.

In accordance with this fixed bed technique, the procedure is carried out in a tubular reactor 1 m long and having an internal diameter of 21 mm. The reactor is charged with 350 cm$^3$ of catalyst having a grain size of 3–5 mm. The reactor is cooled using a system of circulating molten salts, in accordance with well known processes. The temperature of the reactor is then raised and an air/butene mixture is passed into the catalyst bed. The maleic anhydride and butene in the gases leaving the reactor outlet are measured for the purpose of determining the equilibria.

For the purpose of making an evaluation from the catalytic point of view, tests are carried out with the catalysts being investigated, using different operating conditions, the details of which are given in the summary Table II for the tests, further on.

The fact of working with low values for the air/butene ratio brings appreciable gains during the treatment for the recovery of maleic anhydride, quite apart from the gain in selectivity. In actual fact, for the same production capacity gains are obtained in all the steps of the process on account of reduced volumes compared with the previous processes; this reduction applies both to apparatus volumes (cost reductions) and to volumes of fluids being handled (decrease in the necessary power and energy requirements).

Furthermore, the catalyst according to the invention is a low cost catalyst compared with vanadium catalysts, which is reflected in a reduction in operating costs.

We claim:

1. Catalyst for oxidizing organic compounds consisting essentially of, by weight, 80% to 90% titanium dioxide having a specific surface area of between 5 and 20 m$^2$/g as support, the active catalyst components consisting essentially of 8% to 18.5% molybdenum oxide expressed as $MoO_3$, and 1.5% to 5% of an oxide of an added element selected from the group consisting of chromium, antimony, bismuth, iron, nickel, manga-

TABLE I

FLUIDIZED BED OXIDATION

| Catalyst example | Butene to be oxidized | Specific flow rate g of material being oxidized per hour per liter of catalyst | Ratio Air/Butene | Temperature of the bath ° C | Conversion rate % | MAA molar % yield | Selectivity |
|---|---|---|---|---|---|---|---|
| 1 | butene-1 | 270 | 100 | 338 | 89.5 | 32.6 | 38.5 |
| 2 | butene-1 | 270 | 100 | 361 | 97 | 32.9 | 33.5 |
| 3 | butene-1 | 70 | 100 | 450 | 72 | 24 | 52.0 |
| 4 | butene-1 | 70 | 100 | 485 | 84 | 37 | 51.0 |
| 5 | butene-1 | 210 | 33 | 450 | 59.5 | 21.5 | 55.0 |
|   |   | 135 | 51.5 | 450 | 61 | 23.5 | 54.0 |
|   |   | 55 | 125 | 450 | 61 | 21.5 | 55.0 |
| 6 | butene-1 | 70 | 100 | 468 | 84 | 36.5 | 51.5 |
| 7 | butene-1 | 70 | 100 | 484 | 88 | 40.5 | 51.5 |
| 8 | butene-1 | 70 | 100 | 456 | 85 | 38.5 | 52.0 |
| 9 | butene-1 | 70 | 100 | 474 | 86.5 | 38.5 | 53.0 |
| 10 | butene-1 | 70 | 100 | 485 | 63 | 21.5 | 53.0 |
| 11 | butene-1 | 270 | 100 | 448 | 65 | 17 | 28.0 |
|   |   | 270 | 100 | 430 | 59.5 | 16 | 29.0 |

TABLE II

FIXED BED OXIDATION

| Catalysts Example | Material being oxidized butene (B) | Material being oxidized C$_4$ fraction C$_4$[1] | Specific flow rate g of material per hour per liter | Ratio air/butene | Temperature of the bath ° C | Hot point ° C | MAA molar % yield | molar of remaining C$_4$[2] | Selectivity |
|---|---|---|---|---|---|---|---|---|---|
| 5 | B |   | 78 | 130 | 414 | 445 | 46.8 | 0.5 | 48.0 |
| 5 | B |   | 80 | 100 | 417 | 453 | 48.5 | 1.7 | 50.1 |
| 5 | B |   | 100 | 80 | 414 | 455 | 45.6 | 4.5 | 50.0 |
| 5 | B |   | 115 | 70 | 414 | 454 | 45.7 | 6.1 | 51.5 |
| 5 | B |   | 133 | 60 | 414 | 468 | 45.0 | 6.5 | 48.0 |
| 5 | B |   | 160 | 50 | 414 | 468 | 45.0 | 6.1 | 50.0 |
| 5 |   | C$_4$[3] | 95 | 83 | 412 | 439 | 43.8 | 6.5 | 50.0 |
| 12 | B |   | 110 | 100 | 410 | 470 | 48.0[4] | 0.5 | 48.5 |
| 12 | B |   | 160 | 50 | 410 | 485 | 43.0[4] | 0.5 | 43.5 |

[1]. The C$_4$ fraction from the naphtha cracking has the following composition: ethylene + isobutane 2.2%, butane 11.8%, butene-1 54.2%, butene-2 trans 20.7, cis butene-2 9.15 (total butene-1 + butenes-2 84.05%), isobutene 1.9%

[2]. Butene-1 + butenes-2 (cis and trans)

[3]. In this case the calculations are made from the amounts of butene-1, butenes-2 (cis and trans); butane was unchanged; isobutene was converted into acrolein and $CO_2$

[4]. These values fall rapidly, and the catalysts are degraded very quickly during the test.

As is clearly seen in the Tables I and II, it is advantageous to work with an air/butene ratio of less than 100, even though highly favorable results are obtained when operating with ratios greater than 100, which may be of value when using existing installations which have been adapted to work under such conditions.

nese, tungsten and uranium, the atomic ratio of molybdenum to the element added having a value between 1 and 10.

2. Catalyst according to claim 1, in which the materials are present in the amount by weight of 85% to 90% $TiO_2$ support having a specific surface between 5 and 10 m²/g, 8% to 13.5% of molybdenum oxide expressed as MoO₃, 1.5% to 5% of uranium expressed as UO₃, the TiO₂/MoO₃ weight ratio having a value between 7 and 12, and the molybdenum/uranium atomic ratio having a value between 1 and 10.

3. Process for the preparation of a catalyst for oxidizing organic compounds comprising the steps of forming a paste of water, oxalic acid, a molybdenum compound thermally decomposable to molybdenum oxide and titanium dioxide having a specific surface area within the range of 5 to 20 m²/g and an additional metal compound thermally decomposable to the corresponding metal oxide, in which the metal is selected from the group consisting of chromium, antimony, bismuth, iron, nickel, tungsten and uranium, with the materials being present in the ratio of 80–90 parts by weight titanium dioxide, 8–18.5 parts by weight molybdenum oxide expressed as MoO₃, 1.5–5 parts by weight of the additional metal oxide, the atomic ratio of molybdenum to the metal of the additional metal oxide having a value between 1 and 10, drying and calcining the paste.

4. Catalyst as claimed in claim 1 consisting of 85–90% by weight of titanium dioxide, 8–13.5% by weight molybdenum oxide expressed as MoO₃ and 1.5–5% by weight of the oxide of tungsten expressed as WO₃, the TiO₂/MoO₃ weight ratio being between 7 and 12 and the molybdenum-tungsten atomic ratio having a value between 1 and 10.

5. Catalyst as claimed in claim 1 consisting of 85–90% by weight of titanium dioxide, 8–13.5% by weight molybdenum oxide expressed as MoO₃ and 1.5–5% by weight of the oxide of chromium expressed as CrO₃, the TiO₂/MoO₃ weight ratio being between 7 and 12 and the molybdenum-chromium atomic ratio having a value between 1 and 10.

6. Catalyst as claimed in claim 1 consisting of 85–90% by weight of titanium dioxide, 8–13.5% by weight molybdenum oxide expressed as MoO₃ and 1.5–5% by weight of the oxide of nickel, the TiO₂/MoO₃ weight ratio being between 7 and 12 and the molybdenum-nickel atomic ratio having a value between 1 and 10.

7. Catalyst as claimed in claim 1 consisting of 85–90% by weight of titanium dioxide, 8–13.5% by weight molybdenum oxide expressed as MoO₃ and 1.5–5% by weight of the oxide of iron, the TiO₂/MoO₃ weight ratio being between 7 and 12 and the molybdenum-iron atomic ratio having a value between 1 and 10.

8. Catalyst as claimed in claim 1 consisting of 85–90% by weight of titanium dioxide, 8–13.5% by weight molybdenum oxide expressed as MoO₃ and 1.5–5% by weight of the oxide of manganese, the TiO₂/MoO₃ weight ratio being between 7 and 12 and the molybdenum-manganese atomic ratio having a value between 1 and 10.

9. The process as claimed in claim 3 in which the grain size comprises a fraction within the range of 3–5 mm for use of the catalyst in a fixed bed.

* * * * *

UNITED STATES PATENT OFFICE
CERTIFICATE OF CORRECTION

Patent No. 3,994,833　　　　　　　　　Dated　November 30, 1976

Inventor(s)　Marcel Jouy et al

It is certified that error appears in the above-identified patent and that said Letters Patent are hereby corrected as shown below:

column 7, Table II, last column, under "Selectivity", the value　48.5　　　　should be followed by (4).

Signed and Sealed this

Twelfth Day of April 1977

[SEAL]

Attest:

RUTH C. MASON　　　　　　　　　　C. MARSHALL DANN
*Attesting Officer*　　　　　　　　　*Commissioner of Patents and Trademarks*